United States Patent [19]

Gilbert et al.

[11] 4,329,522

[45] May 11, 1982

[54] 1,3,5,7-TETRANITROADAMANTANE AND PROCESS FOR PREPARING SAME

[75] Inventors: Everett E. Gilbert, Morristown, N.J.; Gilbert P. Sollott, Plymouth Meeting, Pa.

[73] Assignee: The United States of America as represented by the Secretary of the Army, Washington, D.C.

[21] Appl. No.: 196,956

[22] Filed: Oct. 14, 1980

[51] Int. Cl.³ .................. C07C 79/08; C07C 76/02
[52] U.S. Cl. ........................... 568/941; 568/942; 149/92; 564/459; 564/461
[58] Field of Search .................. 568/941, 942; 149/92

[56] References Cited

U.S. PATENT DOCUMENTS 3,053,907  9/1962  Smith et al. ................. 568/941
3,258,498  6/1966  Schneider ................... 568/941
3,535,390  10/1970  Driscoll ..................... 568/941

OTHER PUBLICATIONS

C. A. vol. 85, (1976).
Smith, C. W., et al., J. Org. Chem., vol. 26, pp. 2207–2212 (1961).
Stetter, H., et al., Chem. Der., vol. 93, p. 226 (1960).
Stetter, H., et al., Chem. Der., vol. 104, p. 917 (1971).
Kornblum, N., et al., Jacs, vol. 78, p. 4003 (1956).
Kornblum, N., et al., Org. Synthesis, vol. 43, p 87 (1963).
Keinan, et al., J. Org. Chem., vol. 42, p. 844 (1977).
Sollott, G., et al., J. Org. Chem., vol. 45 (26) pp. 5405–5408 (1980).

*Primary Examiner*—Teddy S. Gron
*Attorney, Agent, or Firm*—Nathan Edelberg; Robert P. Gibson; A. Victor Erkkila

[57] ABSTRACT

The invention provides a novel explosive compound 1,3,5,7-tetranitroadamantane, which possesses high explosive energy combined with excellent impact and thermal stability. The novel compound can be prepared by oxidation of 1,3,5,7-tetraaminoadamantane with permanganate.

4 Claims, No Drawings

1,3,5,7-TETRANITROADAMANTANE AND PROCESS FOR PREPARING SAME

GOVERNMENTAL INTEREST

The invention described herein may be manufactured, used and licensed by the Government for governmental purposes without the payment to us of any royalties thereon.

BACKGROUND OF THE INVENTION

Organic nitro compounds have been widely used in the explosives art. Many organic nitro compounds exhibit high explosive energy values, but are relatively sensitive to impact and/or heat. There is a need for organic nitro compounds, which combine high explosive energy values with low thermal and impact sensitivity.

The present invention comprises the novel compound 1,3,5,7-tetranitroadamantane, which exhibits high explosive energy together with excellent impact and thermal stability. Lower nitro derivatives of adamantane have been prepared in the past. Thus, 1-nitro- and 1,3-dinitroadamantanes have been prepared by a tungstate-catalyzed oxidation of the corresponding amino compounds with hydrogen peroxide (G. L. Driscoll, U.S. Pat. No. 3,535,390 (1970)). The nitration of adamantane with concentrated nitric acid in glacial acetic acid at elevated temperature and pressure has been reported to produce 1-nitro-, 1,3-dinitro-, and 1,3,5-trinitroadamantanes, the last in very low yield (G. W. Smith and H. D. Williams, J. Org. Chem. 26, 2207) (1961); U.S. Pat. No. 3,053,907 (1962)). The nitration of alkyladamantanes with nitrogen dioxide at elevated temperature has been reported to yield the 1-nitro- and 1,3-dinitro derivatives (A. Schneider, U.S. Pat. No. 3,258,498 (1966)), while the photochemical reaction of $N_2O_5$ with adamantane yields only mononitration (I. Tabushi et al, Chemistry Letters (Japan), 1431 (1974)).

SUMMARY AND DETAILED DESCRIPTION OF THE INVENTION

The present invention comprises the novel explosive compound 1,3,5,7-tetranitroadamantane and a process for preparing same. The invention also comprises explosive (which term includes propellant) compositions, which contain 1,3,5,7-tetranitroadamantane.

We have found that 1,3,5,7-tetranitroadamantane can be obtained by oxidation of the corresponding tetraamino compound with an oxidizing agent, preferably a soluble permanganate in aqueous medium. This oxidation is a standard one for converting tertiary alkyl amines to the corresponding nitro compounds, but apparently has not been used in the past to prepare compounds containing more than two nitro groups (N. Kornblum, R. J. Clutter and W. J. Jones, J. Am. Chem. Soc. 78, 4003 (1956); N. Kornblum and W. J. Jones, Org. Syntheses 43, 87 (1963)). It has been employed for preparing 1-nitroadamantane (H. Stetter et al, Chem. Ber. 93, 226 (1960); ibid 104, 917 (1971)).

Preferably, the tetraaminoadamantane compound is reacted in aqueous medium with a sufficient amount of a water-soluble permanganate, such as potassium or sodium permanganate, at a temperature in the range of 10° to 60°, especially between 20° and 40°, and advantageously in the presence of acetone to ensure solubilization of the intermediate (forming) nitroadamantanes.

Other oxidizing agents can be utilized in place of permanganate for converting 1,3,5,7-tetraaminoadamantane to the corresponding tetranitro compound, including hydrogen peroxide in the presence of an alkali metal tungstate catalyst (which has been employed for oxidizing mono- and diaminoadamantanes to the corresponding mono- and dinitroadamantanes: U.S. Pat. No. 3,535,390), and ozone in the presence of silica gel (which has been used for oxidizing other amines to nitro compounds: Keinan and Mazur, J. Org. Chem. 42, 844 (1977)).

The following examples provide specific illustrations of the preparation of the novel explosive compound of the present invention:

EXAMPLE 1

Preparation of 1,3,5,7-Tetraacetamidoadamantane

In a one liter quartz reaction flask equipped with a condenser and agitator, 1,3,5,7-tetraiodoadamantane (7.7 g=0.012 mole), prepared according to the process described by R. E. Pincock et al, J. Am. Chem. Soc. 95, 2030 (1973), was stirred briskly in 800 ml of acetonitrile (0.07–0.1% water content) to which 1.0 ml of water had been added. The resulting mixture was photolyzed for 64 hours at approximately 60° C. (ambient temperature) in a Rayonet Photochemical Reactor containing 16 lamps, each lamp approximately 0.03 watt, 1849 angstroms and 2.2 watts, 2537 angstroms (manufacturer's literature, The Southern New England Ultraviolet Co., Middletown, CT). The reaction mixture was filtered to separate the yellowish solids formed, which were then washed with acetonitrile and air-dried. The deep-red acetonitrile filtrate was flash vaporized to remove the acetonitrile. The dark, tarry residue was dissolved in tetrahydrofuran and the pale yellow solids which remained undissolved therein were separated by filtration, washed with tetrahydrofuran solvent and air-dried. The combined solids were dissolved in hot water and the solution was neutralized with aqueous sodium hydroxide and filtered. The filtrate was flash evaporated to dryness. The residue of white solids was washed first with acetone, then with cold water, and finally with acetone and air-dried. 2.68 grams of 1,3,5,7-tetraacetamidoadamantane product were thus obtained, corresponding to a yield of 51% of theory based on the tetraiodo starting material.

The product crystallized from water in the form of needles and analyzed as the tetrahydrate. The product showed no melting to 360° C., which agrees with that reported by H. Stetter and M. Krause, Liebigs Ann. Chem. 717, 60 (1968).

Analysis. Calculated for $C_{18}H_{28}N_4O_4.4H_2O$: C, 49.53; H, 8.31; N, 12.84; O, 29.32; $H_2O$, 16.51%; Mol. wt. 436.5. Found: C, 49.97; H, 8.50; N, 12.46; O, 29.33; $H_2O$ (by weight loss), 16.23%; Mol. wt. (in $H_2O$), 421.

EXAMPLE 2

Preparation of 1,3,5,7-Tetraaminoadamantane Tetrahydrochloride 1,3,5,7-Tetraacetamidoadamantane tetrahydrate (2.0 g=4.6 mmoles) was dissolved in 18% hydrochloric acid (30 ml of concentrated hydrochloric acid diluted with 30 ml of water) and the solution was refluxed for three hours. The crystalline product thus obtained was separated from the mixture by filtration, washed with acetone and dried. 1.29 g of product, mp 360° C. (lit.>360° C., H. Stetter and C. Wulff, Chem. Ber. 93, 1366 (1960)), corresponding to an 82.0% yield, were obtained.

Analysis. Calculated for $C_{10}H_{20}N_4 \cdot 4HCl$: C, 35.11; H, 7.07; N, 16.36. Found: C, 35.35; H, 7.17; N, 16.01.

EXAMPLE 3

Preparation of 1,3,5,7-Tetranitroadamantane 1,3,5,7-Tetraaminoadamantane tetrahydrochloride (5.2 g=0.015 mole) was dissolved in 200 ml of water, and converted to the free base by addition of an equivalent amount of aqueous sodium hydroxide. Magnesium sulfate (10.5 g=0.087 mole) was added to the agitated mixture at 30° C. The mixture was then diluted with 150 ml of acetone and potassium permanganate (57.0 g=0.35 mole) was added portionwise with agitation during 30 minutes. The reaction mixture was agitated at 30° C. for 48 hours and then filtered. The filter cake was washed with water, then dried and extracted eight times with boiling toluene (total amount 400 ml). The combined extracts were filtered, concentrated to a volume of approximately 75 ml and allowed to stand for three days at room temperature. The crystallized solids thus obtained were separated by filtration and dried, yielding 1.27 g of product in the form of truncated square pyramidal crystals, mp>360° C. (dec.). The filtrate yielded an additional 0.87 g of product for a total yield of 2.14 g, 45% of theory. For analysis, a sample of the product was dissolved in acetone and precipitated from solution by the addition of water. The dry product had the following properties: mp 361°–363° C. (decomposed); NMR (DMSO—$D_6$) $\delta 2.92$ (s) relative to TMS; mass spectrum, m/e 270 $(M-NO_2)^+ 100\%$, m/e 178 $(M-3NO_2)^+ 91.5\%$; IR (KBr) 1542, 1362 cm$^{-1}$ ($NO_2$).

Elem. Anal. Found: C, 38.30; H, 3.86; N, 17.50%. Calculated for $C_{10}H_{12}N_4O_8$: C, 37.98; H, 3.83; N, 17.72%.

The foregoing data prove that the product is 1,3,5,7-tetranitroadamantane. Thus, the infrared spectrum showed peaks for nitro groups in the expected range (1362 and 1542 cm$^{-1}$). The NMR spectrum showed only one type of proton, as expected. The mass spectrum was consistent with a structure containing four nitro groups, and with the molecular weight of the compound. The elemental analysis agreed closely with the calculated values.

The novel compound was subjected to the following tests with the results as shown:

Five Second Explosion Temperature: 400° C. This test is described in the *Encyclopedia of Explosives and Related Items*, by B. T. Fedoroff and O. E. Sheffield, Vol. 4 (1969), page D583 et seq. TNT also has a value of 400° C. in this test, but other NATO explosives are in the range of 223° to 287° C. 1,3,5,7-Tetranitroadamantane thus resembles TNT in that it possesses excellent thermal stability.

Impact Sensitivity: "No-go" in the range of 150–240 cm. This test ("ERL Type 12 Tooling") is described in the "Manual of Sensitiveness Tests", G. R. Walker, Ed., Canadian Armament Research and Development Establishment, February 1966, page 15. TNT has a value of 65±5 cm in this test. Accordingly, the novel compound is desirably insensitive to impact and hence is much safer to handle than TNT and many other explosives.

Heat of Combustion: 3952 cal/gm versus 3750 cal/gm for TNT. The calculated detonation pressure for the novel compound is 190 kilobars as compared with 207 kilobars for TNT.

Detonation: A 36-mg. sample was pressed at a loading pressure of 11 KPSI into a steel washer, 0.125" and 0.125" thick. The sample, in the washer, was placed on a 1"×1"×½" steel block, and initiated by an XM70 electrically fired detonator (Picatinny Arsenal Technical Report No. 3209, "Development of TX6025 and XM70 Electric Detonators", Ruth Trezona, Dec. 1964) A dent was produced in the block 0.010" deep, and the washer was enlarged to 0.177" ID, indicating that a high order detonation had occurred. (A blank test using an inert powder with the same detonator produced a dent 0.0085" deep, and no enlargement of the washer.)

The novel explosive compound of the present invention, 1,3,5,7-tetranitroadamantane, can be employed alone as a high explosive. Further, it can be mixed with other high energy explosives, such as TNT, RDX, HMX, etc., which are relatively sensitive to heat and impact, to reduce the impact and thermal sensitivity of such explosives. It can be employed, for example, as the main or complementary explosive charge in projectiles, and as a component of propellant charges for missiles and rockets. For example, U.S. Pat. No. 3,535,390 discloses solid fuels for rockets containing dinitroadamantanes in admixture with ammonium nitrate or ammonium perchlorate. The compound of the present invention is much more efficient energetically than the dinitroadamantanes and hence is more effective for such use.

The foregoing disclosure and drawings are merely illustrative of the principles of this invention and are not to be interpreted in a limiting sense. I wish, it to be understood that I do not desire to be limited to the exact details of construction shown and described, because obvious modifications will occur to a person skilled in the art.

We claim:

1. As a new composition of matter, 1,3,5,7-tetranitroadamantane.

2. A process for preparing 1,3,5,7-tetranitroadamantane which comprises reacting 1,3,5,7-tetraaminoadamantane with an oxidizing agent.

3. The process of claim 2, wherein the oxidizing agent is soluble permanganate in aqueous medium.

4. The process of claim 3, wherein the permanganate is potassium permanganate.

* * * * *